(12) United States Patent
Kinnunen

(10) Patent No.: US 10,105,095 B2
(45) Date of Patent: Oct. 23, 2018

(54) METHOD AND SYSTEM FOR DEFINING BALANCE BETWEEN PHYSICAL ACTIVITY AND REST

(71) Applicant: Oura Health Oy, Oulu (FI)

(72) Inventor: Hannu Kinnunen, Oulu (FI)

(73) Assignee: Oura Health Oy, Oulu (FI)

( * ) Notice: Subject to any disclaimer, the term of this patent is extended or adjusted under 35 U.S.C. 154(b) by 335 days.

(21) Appl. No.: 14/953,752

(22) Filed: Nov. 30, 2015

(65) Prior Publication Data

US 2017/0150918 A1 Jun. 1, 2017

(51) Int. Cl.
*A61B 5/00* (2006.01)
*A61B 5/11* (2006.01)

(52) U.S. Cl.
CPC .......... *A61B 5/486* (2013.01); *A61B 5/1118* (2013.01)

(58) Field of Classification Search
CPC ....... A61B 5/11; A61B 5/1118; A61B 5/1123; A61B 5/486
See application file for complete search history.

(56) References Cited

U.S. PATENT DOCUMENTS

| | | | | |
|---|---|---|---|---|
| 9,352,207 B2* | 5/2016 | Balakrishnan | ....... | A61B 5/7246 |
| 9,414,784 B1* | 8/2016 | Berme | ................ | G06F 19/345 |
| 9,691,253 B2* | 6/2017 | Russell | ............. | G08B 21/0446 |
| 9,795,324 B2* | 10/2017 | Sales | ..................... | A61B 5/1114 |
| 9,848,823 B2* | 12/2017 | Raghuram | ............ | A61B 5/486 |

* cited by examiner

*Primary Examiner* — Max Hindenburg
(74) *Attorney, Agent, or Firm* — Ziegler IP Law Group, LLC

(57) ABSTRACT

Disclosed is a method for defining a balance between physical activity and rest for a user. The method comprises collecting sensor data indicative of a measure of activity performed and rest taken by the user as a function of time; analyzing the sensor data to distinguish sedentary stages from stages of activity or rest; assigning a level to a given stage of activity or rest; evaluating a plurality of activity-rest parameters for the user; and calculating an activity-rest score from the plurality of activity-rest parameters, so as to provide a feedback indicating a status of the balance between the physical activity and the rest.

22 Claims, 3 Drawing Sheets

METHOD AND SYSTEM FOR DEFINING BALANCE BETWEEN PHYSICAL ACTIVITY AND REST

TECHNICAL FIELD

The present disclosure relates generally to health monitoring devices; and more specifically, to a method and system for defining a balance between physical activities performed and rest taken by a user.

BACKGROUND

Recent consumer's interest in personal health has led to a variety of personal health monitoring devices being offered on the market. For example, wearable devices for monitoring personal health are well known in the art. Typically, such devices measure amount of physical activities performed by the user, for example, counts number of steps taken by the user in a day. Further, such devices may measure amount of energy spend (or consumed) by the user while doing such physical activities. Also, such devices may measure level of physical activities performed by the user, for example high, medium or low level of physical activities based on the energy consumption.

However, the current devices do not help in correlating and managing the amount of physical activities performed and the amount of rest taken by the user. In other words, the current devices do not let the user know whether he or she is overtraining or under-training in order to achieve personal target in a healthier way (i.e. by maintaining a balance between the physical activity and rest). Further, the current devices cannot motivate active user to set higher fitness target in the healthier way i.e. by maintaining the balance between the physical activity and the rest. Moreover, the current devices cannot give automatic feedbacks and guidelines, to the user, on how to improve the fitness target when both the physical activity and the rest are taken into consideration.

Therefore, in light of the foregoing discussion, there exists a need to overcome the aforementioned drawbacks of conventional wearable health monitoring devices.

SUMMARY

The present disclosure seeks to provide a method for defining a balance between physical activity and rest for a user.

The present disclosure also seeks to provide a system for defining a balance between physical activity and rest for a user.

The present disclosure further seeks to provide a computer program product that enables in defining a balance between physical activity and rest for a user.

In one aspect, an embodiment of the present disclosure provides a method for defining a balance between physical activity and rest for a user, the method comprising:
collecting sensor data indicative of a measure of activity performed and rest taken by the user as a function of time, wherein the sensor data is collected using at least one sensor of a device worn by the user;
analyzing the sensor data to distinguish sedentary stages from stages of activity or rest;
assigning a level to a given stage of activity or rest, wherein the assigning the level comprises
 (i) assigning a high intensity level to the given stage of activity or rest, when the intensity of activity exceeds a first threshold of intensity,
 (ii) assigning a medium intensity level to the given stage of activity or rest, when the intensity of activity lies between the first threshold of intensity and a second threshold of intensity, wherein the first threshold of intensity is greater than the second threshold of intensity, and
 (iii) assigning a very-low intensity level to the given stage of activity or rest, when the intensity of activity does not exceed the second threshold of intensity;
evaluating a plurality of activity-rest parameters for the user, wherein the plurality of activity-rest parameters comprise at least one of
 (a) a number of recovery days within a first predetermined time period, wherein a recovery day is a day when time spent in activities of the high intensity level does not exceed a first threshold time and/or time spent in activities of the medium intensity level does not exceed a second threshold time, and
 (b) a number of days elapsed from most recent recovery day; and
calculating an activity-rest score from the plurality of activity-rest parameters, so as to provide a feedback indicating a status of the balance between physical activity and rest.

In another aspect, an embodiment of the present disclosure provides a system for defining a balance between physical activity and rest for a user, the system comprising:
a sensor unit for collecting sensor data indicative of a measure of activity performed and rest taken by the user as a function of time, wherein the sensor data is configured to be collected when the sensor unit is worn by the user; and
a data processing arrangement coupled in communication with the sensor unit, wherein the data processing arrangement is configured to
 analyze the sensor data to distinguish sedentary stages from stages of activity or rest,
 assign a level to a given stage of activity or rest, wherein when assigning the level, the data processing arrangement is configured to
  (i) assign a high intensity level to the given stage of activity or rest, when the intensity of activity exceeds a first threshold of intensity,
  (ii) assign a medium intensity level to the given stage of activity or rest, when the intensity of activity lies between the first threshold of intensity and a second threshold of intensity, wherein the first threshold of intensity is greater than the second threshold of intensity, and
  (iii) assign a very-low intensity level to the given stage of activity or rest, when the intensity of activity does not exceed the second threshold of intensity,
 evaluate a plurality of activity-rest parameters for the user, wherein the plurality of activity-rest parameters comprise at least one of
  (a) a number of recovery days within a first predetermined time period, wherein a recovery day is a day when time spent in activities of the high intensity level does not exceed a first threshold time and/or time spent in activities of the medium intensity level does not exceed a second threshold time, and
  (b) a number of days elapsed from most recent recovery day, and calculate an activity-rest score from the plurality of activity-rest parameters, so as to provide a feedback indicating a status of the balance between physical activity and rest.

In yet another aspect, an embodiment of the present disclosure provides a computer program product comprising a non-transitory machine-readable data storage medium having stored thereon program instructions that, when accessed by a processing device, cause the processing device to:

receive sensor data indicative of a measure of activity performed and rest taken by a user as a function of time, wherein the sensor data is collected using at least one sensor of a device worn by the user;

analyze the sensor data to distinguish sedentary stages from stages of activity or rest;

assign a level to a given stage of activity or rest by
(i) assigning a high intensity level to the given stage of activity or rest, when the intensity of activity exceeds a first threshold of intensity,
(ii) assigning a medium intensity level to the given stage of activity or rest, when the intensity of activity lies between the first threshold of intensity and a second threshold of intensity, wherein the first threshold of intensity is greater than the second threshold of intensity, and
(iii) assigning a very-low intensity level to the given stage of activity or rest, when the intensity of activity does not exceed the second threshold of intensity, evaluate a plurality of activity-rest parameters for the user, wherein the plurality of activity-rest parameters comprise at least one of
(a) a number of recovery days within a first predetermined time period, wherein a recovery day is a day when time spent in activities of the high intensity level does not exceed a first threshold time and/or time spent in activities of the medium intensity level does not exceed a second threshold time, and
(b) a number of days elapsed from a most recent recovery day; and calculate an activity-rest score from the plurality of activity-rest parameters, so as to provide a feedback indicating a status of the balance between physical activity and rest.

Embodiments of the present disclosure substantially eliminate or at least partially address the aforementioned problems in the prior art, and enables a user to achieve a fitness target by maintaining a balance between physical activity and rest.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, like elements have been indicated by identical numbers.

Embodiments of the present disclosure will now be described, by way of example only, with reference to the following diagrams wherein.

Figure 1:
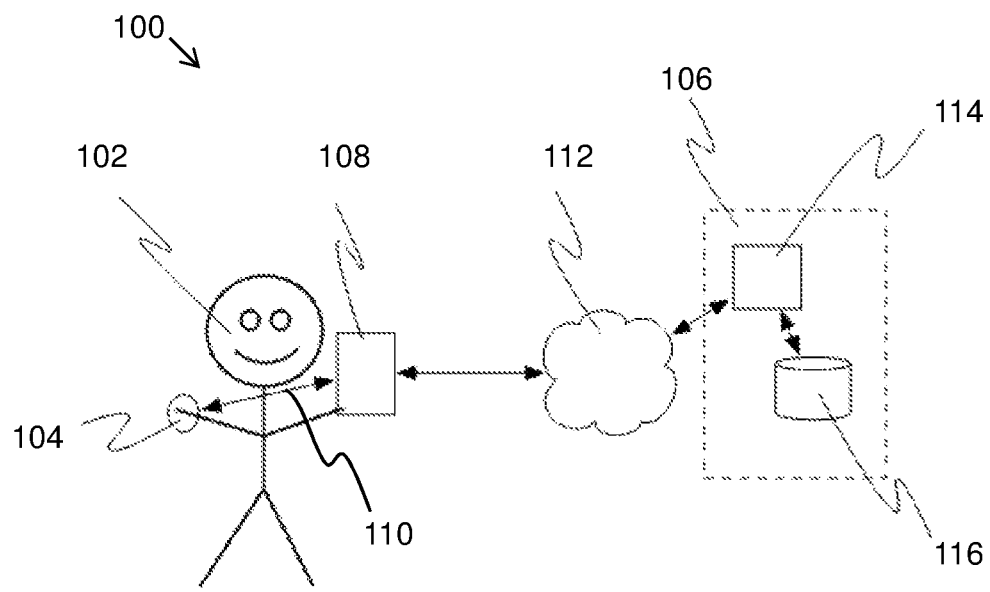
FIG. 1 is a schematic illustration of a system for defining a balance between physical activity and rest for a user, in accordance with an embodiment of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

The terms "connected" or "coupled" and related terms are used in an operational sense and are not necessarily limited to a direct connection or coupling. Thus, for example, two devices may be coupled directly, or via one or more intermediary media or devices. As another example, devices may be coupled in such a way that information can be passed there between, while not sharing any physical connection with one another. Based on the present disclosure provided herein, one of ordinary skill in the art will appreciate a variety of ways in which connection or coupling exists in accordance with the aforementioned definition.

The phrases "in an embodiment", "in accordance with an embodiment" and the like generally mean the particular feature, structure, or characteristic following the phrase is included in at least one embodiment of the present disclosure, and may be included in more than one embodiment of the present disclosure. Importantly, such phrases do not necessarily refer to the same embodiment.

If the specification states a component or feature "may", "can", "could", or "might" be included or have a characteristic, that particular component or feature is not required to be included or have the characteristic.

In one aspect, an embodiment of the present disclosure provides a method for defining a balance between physical activity and rest for a user, the method comprises:

collecting sensor data indicative of a measure of activity performed and rest taken by the user as a function of time, wherein the sensor data is collected using at least one sensor of a device worn by the user;

analyzing the sensor data to distinguish sedentary stages from stages of activity or rest;
assigning a level to a given stage of activity or rest, wherein the assigning the level comprises:
(i) assigning a high intensity level to the given stage of activity or rest, when the intensity of activity exceeds a first threshold of intensity,
(ii) assigning a medium intensity level to the given stage of activity or rest, when the intensity of activity lies between the first threshold of intensity and a second threshold of intensity, wherein the first threshold of intensity is greater than the second threshold of intensity, and
(iii) assigning a very-low intensity level to the given stage of activity or rest, when the intensity of activity does not exceed the second threshold of intensity;
evaluating a plurality of activity-rest parameters for the user, wherein the plurality of activity-rest parameters comprise at least one of:
(a) a number of recovery days within a first predetermined time period, wherein a recovery day is a day when time spent in activities of the high intensity level does not exceed a first threshold time and/or time spent in activities of the medium intensity level does not exceed a second threshold time,
(b) a number of days elapsed from most recent recovery day; and
calculating an activity-rest score from the plurality of activity-rest parameters, so as to provide a feedback indicating a status of the balance between physical activity and rest.

In another aspect, an embodiment of the present disclosure provides a system for defining a balance between physical activity and rest for a user, the system comprises:
a sensor unit for collecting sensor data indicative of a measure of activity performed and rest taken by the user as a function of time, wherein the sensor data is configured to be collected when the sensor unit is worn by the user; and
a data processing arrangement coupled in communication with the sensor unit, wherein the data processing arrangement is configured to:
analyze the sensor data to distinguish sedentary stages from stages of activity or rest;
assign a level to a given stage of activity or rest, wherein when assigning the level, the data processing arrangement is configured to:
(i) assign a high intensity level to the given stage of activity or rest, when the intensity of activity exceeds a first threshold of intensity;
(ii) assign a medium intensity level to the given stage of activity or rest, when the intensity of activity lies between the first threshold of intensity and a second threshold of intensity, wherein the first threshold of intensity is greater than the second threshold of intensity; and
(iii) assign a very-low intensity level to the given stage of activity or rest, when the intensity of activity does not exceed the second threshold of intensity;
evaluate a plurality of activity-rest parameters for the user, wherein the plurality of activity-rest parameters comprise at least one of:
(a) a number of recovery days within a first predetermined time period, wherein a recovery day is a day when time spent in activities of the high intensity level does not exceed a first threshold time and/or time spent in activities of the medium intensity level does not exceed a second threshold time,
(b) a number of days elapsed from most recent recovery day; and
calculate an activity-rest score from the plurality of activity-rest parameters, so as to provide a feedback indicating a status of the balance between physical activity and rest.

In yet another aspect, an embodiment of the present disclosure provide a computer program product comprising a non-transitory machine-readable data storage medium having stored thereon program instructions that, when accessed by a processing device, cause the processing device to:
receive sensor data indicative of a measure of activity performed and rest taken by a user as a function of time, wherein the sensor data is collected using at least one sensor of a device worn by the user;
analyze the sensor data to distinguish sedentary stages from stages of activity or rest;
assign a level to a given stage of activity or rest by:
(i) assigning a high intensity level to the given stage of activity or rest, when the intensity of activity exceeds a first threshold of intensity,
(ii) assigning a medium intensity level to the given stage of activity or rest, when the intensity of activity lies between the first threshold of intensity and a second threshold of intensity, wherein the first threshold of intensity is greater than the second threshold of intensity, and
(iii) assigning a very-low intensity level to the given stage of activity or rest, when the intensity of activity does not exceed the second threshold of intensity;
evaluate a plurality of activity-rest parameters for the user, wherein the plurality of activity-rest parameters comprise at least one of:
(a) a number of recovery days within a first predetermined time period, wherein a recovery day is a day when time spent in activities of the high intensity level does not exceed a first threshold time and/or time spent in activities of the medium intensity level does not exceed a second threshold time,
(b) a number of days elapsed from a most recent recovery day; and
calculate an activity-rest score from the plurality of activity-rest parameters, so as to provide a feedback indicating a status of the balance between physical activity and rest.

According to an embodiment, the present disclosure is associated with a system, having a sensor unit and a data processing arrangement coupled in communication with the sensor unit. In an embodiment, the sensor unit is associated with a wearable electronic device configured to measure user's physiological data. For example, the wearable electronic device may be configured to measure user's movements and a heart rate. Further, the wearable electronic device may be a ring configured to be suitably worn at a finger, such as an index finger. Alternatively, the wearable electronic device may be a device adapted to be worn at wrist, chest and any suitable body part of the user, from where physiological data of the user can be measured. According to an embodiment, the wearable electronic device is as described in PCT/FI2014/000043, which application is hereby incorporated by reference.

In an embodiment, the sensor unit comprises at least one sensor for collecting sensor data associated with the user. For example, the at least one sensor is selected from the group consisting of motion sensors, optical sensors and temperature sensors, capable of measuring various users' parameters.

According to an embodiment, the wearable electronic device also includes other electronic components associated with the sensor unit. For example, the wearable electronic device may include other electronic components which may include but not limited to a microcontroller operable to control operation of the sensors for generating data related to the user's movement, heart rate, temperatures, ambient light and the like.

In one embodiment, the wearable electronic device also comprises a communication interface for communicating the collected sensor data to an external device. The communication interface enables in establishing a communication between the wearable electronic device and the external device for sharing the collected sensor data there-between. For example, the external device may be wirelessly connected to the chargeable device by the communication interface, such as a Wi-Fi, Bluetooth and the like, for collecting the sensor data from the wearable electronic device. In an example, the external device may comprise a computing device, which includes but not limited to a smart phone, a tablet computer, a phablet and a laptop. In an embodiment, the external device enables in at least partially process or analyse the collected sensor data to determine user's physiological data.

In one embodiment, the data processing arrangement coupled in communication with the sensor unit (of the wearable electronic device) may be a processor of the external device (communicably coupled to the wearable electronic device). Alternatively, the data processing arrangement may be a processor of a server which is further communicably coupled to the external device. The server may be operable to at least partially process or analyse the collected sensor data to determine user's physiological data. Additionally, the data processing arrangement may be a microprocessor of the wearable electronic device operable to at least partially process or analyse the collected sensor data. In other words, the data processing arrangement may be associated with at least one of the microprocessor of the wearable electronic device, the processor of the external device and the processor of the server operable to process or analyse the collected sensor data to determine user's physiological data.

The system of the present disclosure enables defining a balance between physical activity and rest for a user. The sensor unit of the system (particularly the wearable electronic device) enables in collecting the sensor data indicative of a measure of activity performed and rest taken by the user as a function of time. Further, as mentioned above, the sensor data is configured to be collected when the sensor unit is worn by the user. In an embodiment, the measure of the activity performed and the rest taken by the user may be performed with movement data. Specifically, the movement data of the user may be collected with the motion sensor of the sensor unit, further the motion sensor data may be correlated with heart rate (or other sensor data of the sensor unit) to measure whether the activity performed by the user and the rest taken by the user. Further, the measure of activity performed and the rest taken by the user is performed as the function of time, i.e. the motion sensor data and the heart rate may be considered for example 1 minute, 10 minutes or 1 hour, to measure whether the activity is performed and rest is taken. For example, if the measured motion sensor data and the heart rate is less (or small value) the user may be considered to be resting, whereas if the measured motion sensor data and the heart rate is more (or large value) the user may be considered doing some activity.

In an embodiment, the activity performed by the user may include but not limited to walking, jogging, running, or doing some kind of exercise. Further, the rest taken by the user may include sedentary, i.e. for example sitting in chair or sofa, and sleeping. In other words, the measured motion sensor data and the heart rate (and other sensor data) may enable in indicating whether the user is doing some activity or in sedentary position or sleeping.

The data processing arrangement (coupled in communication with) the sensor unit is configured to analyze the sensor data to distinguish sedentary stages from stages of activity or rest. The distinction between the activity performed or rest taken by the user may be simply performed, with the help of an algorithm to be executed by at least one of the microcontroller or the processor of the external device or the server, by distinguishing the large values (of the measured motion sensor data and the heart rate) from the small values indicating the activity performed and the rest taken, respectively. However, the distinction of the sedentary stages from the stages of activity or rest may be performed with the help of a motion sensor algorithm, which can separate standing motion data form sitting and lying motion data of the user. For example, the motion sensor may detect that the hand is roughly like 90 degrees to a gravity vector of the earth by detecting 1 g or −1 g signal on its x-axis when the user is in the sedentary state, which separates it from standing situation when 1 g or −1 g is mostly on y-axis. Additionally, the motion sensor may detect minor movements so as to differentiate the user from lying and sleeping, when there is no or only few movements as compared to the movements when the user is simply lying (or sitting).

The data processing arrangement is further configured to assign a level to a given stage of activity or rest. For example, the data processing arrangement is configured to assign a high intensity level to the given stage of activity or rest, when the intensity of activity exceeds a first threshold of intensity. According to an embodiment, the assignment of levels (such a high intensity level) to the activity may be done based on a metabolic equivalent of task (MET), which is a physiological measure expressing the energy cost of physical activities and is defined as the ratio of metabolic rate during a specific physical activity to a reference metabolic rate, such as set by convention to an amount of oxygen ($O_2$) consumed equal to 3.5 ml $O_2$ per kg body weight of the user multiplied by minutes. In an example, the first threshold of intensity, for assignment of the high intensity level to an activity, includes 6 MET or more. In other words, an activity to be assigned as high intensity level (or vigorous) may consume 6 MET or more, which may include running 6 miles per hour (mph) or any other form of vigorous exercise, such as pushups, sit-ups, pull-ups, jumping jacks and the like. It may be evident that the sensor unit may include a sensor capable of measuring $O_2$ consumption and the data processing arrangement may be provided with the weight of the user for determining MET for assignment of intensity levels to the activities.

Further, the data processing arrangement is configured to assign a medium intensity level to the given stage of activity or rest, when the intensity of activity lies between the first threshold of intensity and a second threshold of intensity. Further, the first threshold of intensity is greater than the second threshold of intensity. In an example, the second threshold of intensity may be 3 MET. Therefore, any activity associated with the consumption of minimum 3 MET and maximum of 6 MET may be assigned as medium intensity level activity. In an example, the medium intensity level activity may include but not limited to bicycling less than 10 mph, swimming 0.25 mph or brisk walking (more than 2.0 mph and less than 5 mph).

Moreover, the data processing arrangement is configured to assign a very-low intensity level to the given stage of activity or rest, when the intensity of activity does not exceed the second threshold of intensity.

According to an embodiment, the intensity of activity may be divided into more than three levels. For example, each area listed above may each be diveded into two sub-sets, each including a sub-threshold of intensity. Another example is that the activity below the second threshold of intensity is divided into two, i.e. a low intensity level is added, wherein the low intensity value is assigned to an area lying between the second threshold of intensity and a third threshold of intensity, where the third threshold of intensity is lower than the second threhold of intensity. In an example, the third threshold of intensity may be 1 MET. Therefore, in this embodiment, any activity associated with the consumption of less than 1 MET may be assigned as very-low intensity level activity. In an example, the very-low intensity level activity may include sleeping.

According to an embodiment, the data processing arrangement is thus further configured to assign a low intensity level to the given stage of activity or rest, when the intensity of activity is between the second and third threshold of intensity (i.e. between 1 MET to 3 MET). Therefore, in an example, the low intensity level activity may include but not limited to sitting, watching television, simply lying on bed, writing, doing desk work, typing, simply standing or even walking less than 2.0 mph. Similarly, the data processing arrangement may be configured to assing a very high intensity level to a given stage of activity, when the intensity of activity is above a fourth threshold of intensity. The fourth threshold would then be higher than the first threshold and the high intensity level would then be between the fourth and the first threshold of intensity. It may also be possible for the user to set these additional intensity level thresholds, depending on his/her usual activies and personal goals.

The data processing arrangement is further configured to evaluate a plurality of activity-rest parameters for the user. The activity-rest parameters for the user primarily depends on amount of activity performed and rest take. The activity-rest parameters also depend on the measure of the level of activity or rest, i.e. the high, medium, low and very-low intensity of activities.

The plurality of activity-rest parameters comprise a number of recovery days within a first predetermined time period. In an embodiment, the first predetermined time period is selected from the group consisting of last three days, last seven days, last 10 days, last two weeks and last month. Further, a recovery day is a day when time spent in activities of the high intensity level does not exceed a first threshold time and/or time spent in activities of the medium intensity level does not exceed a second threshold time.

In one embodiment, the first threshold time may include 100 MET minutes, i.e. when the user has not performed the high intensity level activities for more than 17 minutes (100/6=16.7). Therefore, the number of recovery days includes number of days (for example in the last seven days, i.e. the first predetermined time period) when the user has performed the high intensity level activity (i.e. more than 6 MET, but less than 17 minutes) and still do not require rest for recovery. In an embodiment, the second threshold time may include 200 MET minutes, i.e. when the user has not performed the medium intensity level activities for more than 67 minutes (200/3=66.7 minutes). Therefore, the number of recovery days also include number of days (for example in the last seven days) when the user has performed the medium intensity level activity (i.e. is more than 3 MET, but less than 67 minutes) and do not require rest for recovery. Accordingly, the number of recovery days may be calculated as number of days during the last week when the activities performed by the user has not exceeded above the first threshold time (of 100 MET minutes) and the second threshold time (of 200 MET minutes).

The plurality of activity-rest parameters also comprise a number of days elapsed from the most recent recovery day. In other words, the number of days elapsed includes days since when the last recovery day has been, i.e. the days since when at least the first and/or second threshold times has not exceeded. The number of days elapsed enable in finding a recovery day. In an example, a maximum number of days elapsed may be 9 days.

According to an embodiment, the criteria of activity day and/or recovery day may be configured to vary depending on the quality and quantity of sleep measured the previous recovery period, typically the previous night. Such an embodiment would take into account the fact that a badly-rested person is more easily stressed than a well-rested person.

In one embodiment, the plurality of activity-rest parameters further comprise time spent in sedentary stages during a second predetermined time period. For example, the second predetermined time period is selected from the group consisting of last 24 hours, last 48 hours and last 72 hours. The time spent in sedentary stages is an amount of time the user is in a sedentary position, for example merely sitting for resting or sitting for doing some desk oriented job such as writing, typing, taking phone call and the like. In one example, the time spent in the sedentary stages may be calculated as time, i.e. minute by minute when the person is in the sedentary position in one day. Alternatively, the time spent in the sedentary stages may also consider one or more previous days and averaged to represent one day. Further, different days may be weighted also so that last day may have 50%, previous day may be 35%, the day before may be 20% weighting.

In one embodiment, the plurality of activity-rest parameters further comprise a number of sedentary alerts received during the second predetermined time period. In an example, a sedentary alert may correspond to a maximum time, of about 1 hour, constantly spent in the sedentary position. Therefore, the number of sedentary alerts may be number of times (when the user is in more than 1 hour in the sedentary position) in the second predetermined time period, for example in last 24 hours. In an embodiment, the wearable electronic device may be configured to make some sounds (for example beeps) to provide the sedentary alert, alternatively the sedentary alert may be provided to the user on the external device (for example in the smart phone) as a message or sound. Therefore, the sedentary alerts enable in motivating the user to move when he or she is sitting for long time.

In one embodiment, the plurality of activity-rest parameters further comprise a number of days, within the first predetermined time period, when the user has achieved a preset activity target. In an example, the preset activity target may include walking 10000 steps in a day. Therefore, the number of days when the user has achieved the preset activity target may be the number of days during the last seven days when the user has reached walked 10000 steps. In other words, the wearable electronic device counts steps over one day (time −00:00:00-24:00:00), and if the user completes 10000 steps that particular day may be assigned a value of 1 otherwise that day may be assigned a value of 0. Therefore, at the end of seven days, the number of days (when the user has achieved the preset activity target) may include a value from 0 to 7.

In one embodiment, the plurality of activity-rest parameters further comprises a sum of a first integral of a measure of intensity over time for activities of the high intensity level performed during the first predetermined time period and a second integral of the measure of intensity over time for activities of the medium intensity level performed during the first predetermined time period. In other words, the first integral of the measure of intensity over time (for activities of the high intensity level performed during the first predetermined time period) is sum of time, for example, in minutes for which the user has performed activities of the high level intensity (i.e. more than 6 MET) in the last seven days. Similarly, the second integral of the measure of intensity over time (for activities of the medium intensity level performed during the first predetermined time period) is sum of time, for example in minutes for which the user has performed activities of the medium level intensity (i.e. more than 3 MET) in the last seven days. Therefore, the sum of the first and second integrals includes a sum of time (for example in minutes) for the last seven days in which the user has performed activities of both the high and medium level intensities.

In one embodiment, the plurality of activity-rest parameters further comprise a number of days, within the first predetermined time period, when the sum of the first and second integrals exceeds a threshold value. In an example, the threshold value may be 100 MET minutes. The number of days (when the sum of the first and second integrals exceeds the threshold value, in the first predetermined time period) includes number of days in last seven days (or a week) when a sum of energy consumption in activities of the high and medium level intensities is more than 100 MET minutes.

In may be evident, that the plurality of activity-rest parameters may also include sleeping time. As mentioned above, the sleeping (i.e. very-low activity) time may be calculated using the motion sensor data and the heart rate measurement. In other words, the sleeping time may correspond to a time the user is subjected to consumption of less than 1 MET.

According to an embodiment, the data processing arrangement is further configured to evaluate the plurality of activity-rest parameters based upon at least one of: an age of the user, a gender of the user, a weight of the user, a height of the user. It may be evident that the activity-rest parameters may be depended (or associated) with the age of the user, the gender of the user, the weight of the user and the height of the user. Accordingly, when a user is evaluated on the basis of the activity-rest parameters (by the data processing arrangement) such aspects may be considered. In other words, each of the plurality of activity-rest parameters may include a weightage (or factor) depending on the age, gender, weight and height of the user, and when such plurality of activity-rest parameters are evaluated these factors are taken into consideration, which may be different for different user. In an example, for a young user the evaluation of the plurality of activity-rest parameters would be stricter or tougher as compared to an aged user. A specific example would be that the preset activity target for a young user may be 10000 steps in a day which may be equivalent to 9000 steps in a day for an aged user. In this case, the factor may be the preset activity target of an aged user=0.9 of the preset activity target of a young user. Similarly, the gender, weight and height of the users may be also taken into consideration while evaluating the plurality of activity-rest parameters thereof.

The data processing arrangement is further configured to calculate an activity-rest score from the plurality of activity-rest parameters, so as to provide a feedback indicating a status of the balance between physical activity and rest. The activity-rest score is an indicator of the balance between physical activity and rest. For example, higher the activity-rest score better is the balance between physical activity and rest.

According to an embodiment, at least one of the plurality of activity-rest parameters contributes positively to the activity-rest score, and at least one of the plurality of activity-rest parameters contributes negatively to the activity-rest score. For example, the activity-rest parameters, such as the number of days when the user has achieved the preset activity target and the sum of the first and second integrals of time over activities of the high and medium intensity levels, contributes positively to the activity-rest. However, the activity-rest parameters, such as the time spent in sedentary stages and the number of sedentary alerts, contributes negatively to the activity-rest score.

According to another embodiment, the activity-rest score may depend linearly on at least one of the plurality of activity-rest parameters. Further, the activity-rest score may depend non-linearly on at least one of the plurality of activity-rest parameters. It may be evident that performance score of each of the plurality of activity-rest parameters may not have equal affect on the final activity-rest score, therefore each of the plurality of activity-rest parameters may be assigned different weightages based on their affect. Therefore, some of the plurality of activity-rest parameters contributes linearly and some non-linearly (based on weightages associated therewith) for the calculation of the activity-rest score.

According to an embodiment of the present disclosure, the following seven activity-rest parameters, i.e. the number of recovery days, the number of days elapsed from most recent recovery day, the time spent in sedentary stages, the number of sedentary alerts, the number of days when the user has achieved the preset activity target, the sum of the first and second integrals of the measure of intensity over time for activities of the high and medium intensity levels performed, and a number of days when the sum of the first and second integrals exceeds the threshold value, may be taken into consideration for calculation of the activity-rest score.

In one embodiment, each of the seven activity-rest parameters may include performance score, calculated by associating limits of the activity-rest parameters with an achieved target, and represented with percentage. For example, the activity-rest parameter such as the number of days (when the user has achieved the preset activity target) may include Limits [0 1 5 6] and their corresponding performance score may include percentage value of [0, 25, 95, 100]. Specifically, if the number of days (when the user has achieved the preset activity target) is 6 or 7 days (6 days being considered as a target for a week) then the parameter, i.e. the number of days when the user has achieved the preset activity target, contributes 100%. Similarly, if the number of days (when the user has achieved the preset activity target) is 5 days then the parameter, i.e. the number of days when the user has achieved the preset activity target, contributes 95%. Further, if the number of days (when the user has achieved the preset activity target) is 1 day then the parameter, i.e. the number of days when the user has achieved the preset activity target, contributes 25%. Moreover, if the number of days (when the user has achieved the preset activity target) is 2 days then the parameter, i.e. the number of days when the user has achieved the preset activity target, contributes 42.5%.

Similarly, performance score of the other activity-rest parameters may be calculated to contribute to calculate activity-rest score. For example, if the parameter, i.e. number of days when the user has achieved the preset activity target=[0 1 5 6] (for example number of days per week), the corresponding parameter, i.e. time spent in sedentary stages=[960 720 420 300] (for example number of minutes per day or 24 hours). Similarly, other corresponding performance score of the remaining activity-rest parameters may be, the number of sedentary alerts=[10 5 1 0] (for example, number of alerts in a day); the sum of the first and second integrals of the measure of intensity over time for activities of the high and medium intensity levels performed=[0 150 750 2000] (for example, number of minutes per week); the number of days when the sum of the first and second integrals exceeds the threshold value [0 0.5 3 4] (for example, number of days per week); the number of recovery days=[0 0.5 1 2] (for example number of days per week); and the number of days elapsed from a most recent recovery day [9 7 3 2].

As mentioned, the performance score of the activity-rest parameter, i.e. number of days when the user has achieved the preset activity target=[0 1 5 6] corresponds to [0%, 25%, 95%, 100%]. Similarly, the performance of the other activity-rest parameters may be expressed in terms of weighted percentage to calculate the activity-rest score. For example, the contributing percentage corresponding to each of the four elements of the seven vectors (vector performance scores) may be considered to calculate the activity-rest. In an example, the activity score is the average of the seven weighted parameters scores, i.e.

Activity-rest score=performance scores of [number of recovery days+number of days elapsed from most recent recovery day+time spent in sedentary stages+number of sedentary alerts+number of days when the user has achieved the preset activity target+sum of the first and second integrals of the measure of intensity over time for activities of the high and medium intensity levels performed+number of days when the sum of the first and second integrals exceeds the threshold value]/7

As mentioned above, the feedback enables in indicating the status of the balance between physical activity and rest. Specifically, the activity-rest score (calculatedac with the help of the plurality of activity-rest parameters) enables in indicating the status of the balance between physical activity and rest. In an example, the activity-rest score may be represented with a percentage count associated with a feedback for the status of the balance between physical activity and rest. In an example, when the activity-rest score is about 35%, the feedback for such status of balance between physical activity and rest may be that "you need to take actions to improve your physical activity". Further, when the activity-rest score is between 35%-70%, the feedback for such status of balance between physical activity and rest may be that "you could pay attention to your physical activity behaviour". Furthermore, when the activity-rest score is between 70%-85%, the feedback for such status of balance between physical activity and rest may be that "your physical activity patterns lately are somewhat below recommended levels, apparently yet maintaining your health and wellbeing". Moreover, when the activity-rest score is between 85%-100%, the feedback for such status of balance between physical activity and rest may be that "on this day and previous week, you have been following general recommendations regarding physical activity to the level that most probably improves your health and fitness". In such instance, the user may further increase the physical activity (and levels thereof) to further enhance his or her fitness and still try to balance the physical activity and rest with the help of calculated activity-rest score.

In an embodiment, the activity-rest score may be provided to the user in a display (coupled to the data processing arrangement) of the external device associated with the user. The data processing arrangement is further configured to render the feedback on the display, so as to enable the user to see his/her performance with respect to each of the plurality of activity-rest parameters. In other words, the data processing arrangement is configured to render the activity-rest score, the performance with respect to each of the plurality of activity-rest parameters and the feedback corresponding to the activity-rest score in the display of the external device.

In one embodiment, the data processing arrangement is further configured to enable the user to simulate how the activity-rest score changes when a given activity-rest parameter is changed. For example, each of the activity-rest score and the performance score with respect to each of the plurality of activity-rest parameters may be provided (or rendered) on the display with the help of a movable slidable bar. Therefore, by moving the at least one of the movable slidable bar associated with at least one of the performance score of the plurality of activity-rest parameters enables the user to simulate how the activity-rest score changes when a given activity-rest parameter is changed. Additionally, by moving the movable slidable bar associated the activity-rest score the user may simulate how the performance score of the plurality of activity-rest parameters may be changed when a given activity-rest score is changed.

The present disclosure provides a system and a method for enabling a user to achieve a fitness target by maintaining a balance between physical activity and rest. The present disclosure enables in correlating and managing the amount of physical activities performed and the amount of rest taken by the user. This allows the user to know whether he or she is overtraining or under-training in order to achieve his or her personal fitness target in a healthier way (i.e. by maintaining a balance between the physical activity and the rest). Further, the present disclosure enables in motivating users to set even higher fitness targets but still managing and maintaining the balance between the physical activity and rest. Moreover, the present disclosure provides automatic feedbacks and guidelines, to the user, on how to improve the fitness target by still managing and maintaining the balance between the physical activity and rest.

DETAILED DESCRIPTION OF THE DRAWINGS

Referring to FIG. 1, illustrated is a schematic illustration of a system 100 for defining a balance between physical activity and rest for a user 102, in accordance with an embodiment of the present disclosure. As shown, a wearable electronic device 104 is worn by the user 102. The wearable electronic device 104 includes a sensor unit (not shown) for collecting sensor data indicative of a measure of activity performed and rest taken by the user 102 as a function of time. The system 100 also includes a data processing arrangement 106 coupled in communication with the sensor unit of the wearable electronic device 104. As shown, the wearable electronic device 104 is communicably coupled to an external device 108 using a communication network 110, such as Wi-Fi or Bluetooth. The external device 108 is further communicably coupled to the data processing arrangement 106 via a communication network 112.

The collected sensor data is communicated via the external device 108 to the data processing arrangement 106 via the communication network 112. The data processing arrangement 106 is a server having a processor 114 for analyzing the collected sensor data. The analysis of the collected sensor data can be also partially done by a microcontroller (not shown) of the wearable electronic device 104 and a processor (not shown) of the external device 108. The data processing arrangement 106 also includes a database 116 for storing the collected sensor data and the analysed sensor data. The data processing arrangement 106 is configured to calculate an activity-rest score from a plurality of activity-rest parameters, of the user 102, associated with the collected sensor data and the analysed sensor data. The user 102 can access the calculated activity-rest score thereof on a display of the external device 108. The display of the external device 108 renders graphical representations of the activity-rest score and performance of the associated activity-rest parameters.

Figure 2A:
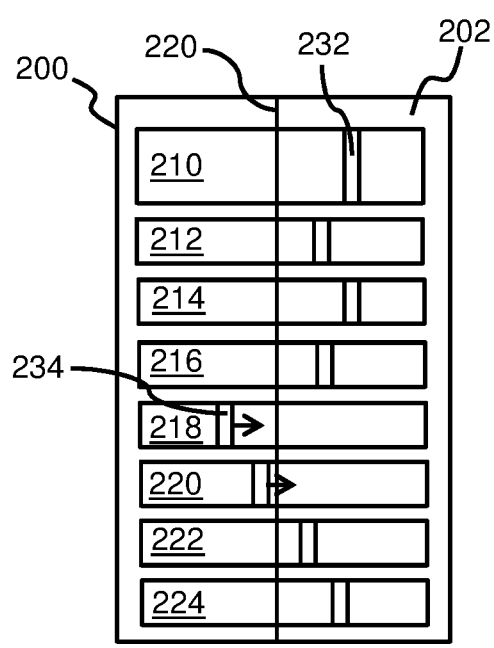
FIGS. 2A-B are schematic illustrations of user interfaces to be rendered on a display of an external device, in accordance with an embodiment of the present disclosure.
Figure 2B:
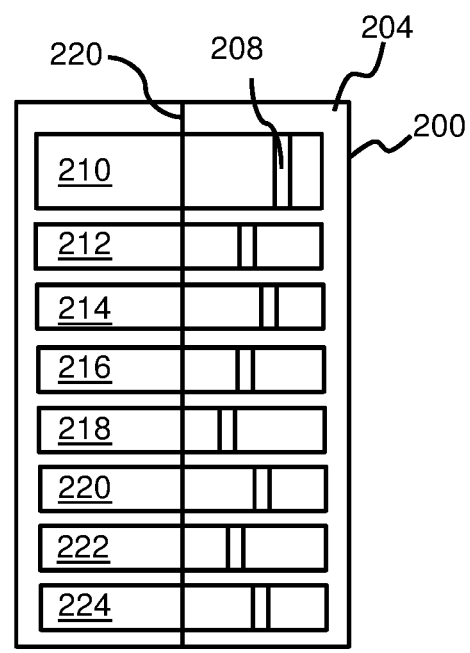

Referring now to FIGS. 2A-B, illustrated are schematic illustrations of user interfaces to be rendered on a display 200 of an external device (such as the external device 108 for example smart phone), in accordance with an embodiment of the present disclosure. As shown, FIG. 2A illustrates a user interface 202 depicting an activity-rest score 210 and performance score of corresponding or related activity-rest parameters. Specifically, the user interface 202 depicts performance scores associated with and considered for calculation of the activity-rest score 210. As shown the, the performance scores are corresponding to the activity-rest parameters which is includes number of recovery days 212, number of days elapsed from most recent recovery day 214, time spent in sedentary stages 216, number of sedentary alerts 218, number of days when the user has achieved the preset activity target 220, sum of first and second integrals of a measure of intensity over time for activities of a high and medium intensity levels performed 222, and a number of days when the sum of the first and second integrals exceeds a threshold value 224.

The user interface 202 also includes a neutral value indicator 220 for the activity-rest score 210 and the performance score of the activity-rest parameters 212-224. The values on left of the neutral value indicator 220 are considered to be negative values (indication, when set target is not reached) and values on the right of the neutral value indicator 220 is considered to be positive values (indication, when set target is reached). Further, each of the activity-rest score 210 and the performance score of the activity-rest parameters 212-224 are indicated with the help of a movable slidable bar, such as a slidable bar 232 and 234. The user can simulate how the activity-rest score 210 changes when at least one of performance score of the activity-rest parameters 212-224 is changed. For example, the activity-rest score 210 can be changed by moving the slidable bar 234. The user interface 202 may also include a feedback (not shown) indicating a status of the balance between physical activity and rest.

Referring now to FIG. 2B, illustrated is the display 200 rendered with another user interface 204. The user interface 204 depicts a change in the activity-rest score 210 when the performance score of the activity-rest parameters 218-220 (which were on the left of the neutral value indicator 220, as shown in FIG. 2A) are changed. Specifically, the slidable bars, such as the slidable bar 234 are moved from left to right side of the neutral value indicator 220 for changing the activity-rest score 210. This enables the user to improve the performance score of the activity-rest parameters 218-220 for overall increase of the activity-rest score 210. Further, the slidable bar 232 of the activity-rest score 210 may also configured to be moved for simulating corresponding change in the performance score of the activity-rest parameters 212-224. The enables a user (such as the user 102) to know the required performance score of the activity-rest parameters 212-224 to be attained for attaining the set activity-rest score 210.

Figure 3:
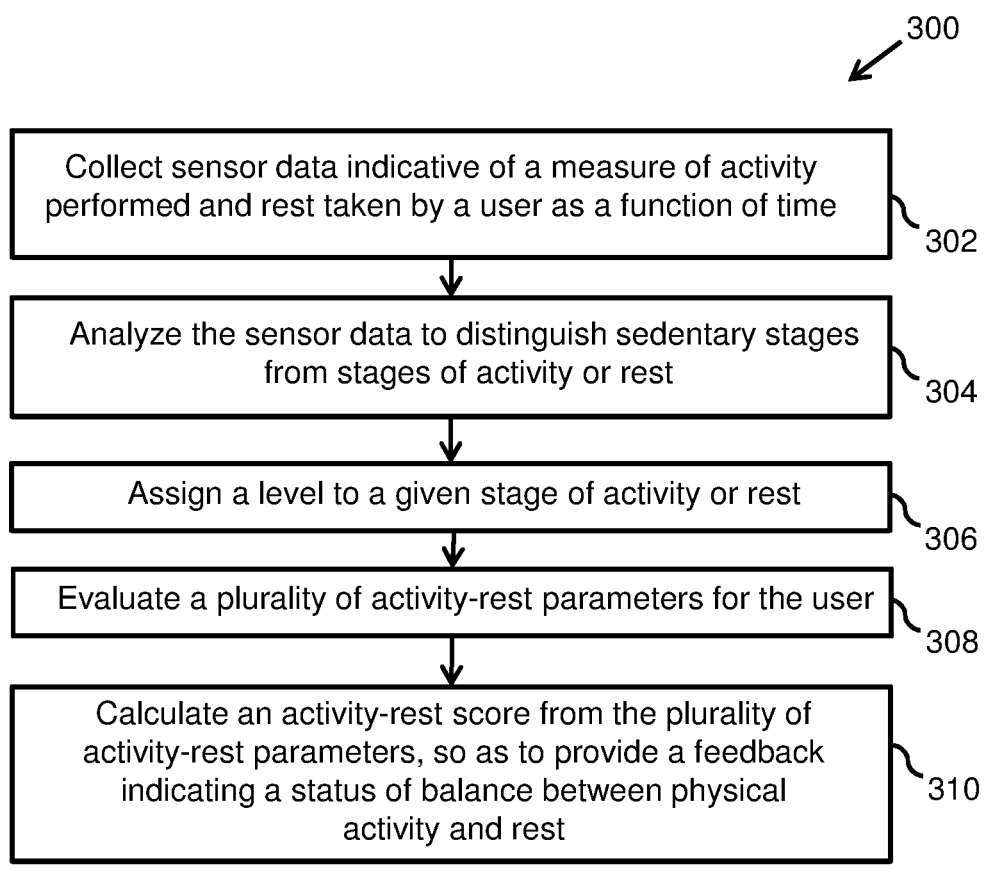
FIG. 3 is an illustration of steps of a method for defining the balance between physical activity and rest for the user, in accordance with an embodiment of the present disclosure.

Referring now to FIG. 3, illustrated are steps of a method 300 for defining a balance between physical activity and rest for a user, in accordance with an embodiment of the present disclosure. Specifically, those skilled in the art would recognize that the method 300 illustrates steps involved in the operation of the system 100, explained in conjunction with the FIGS. 1-2.

At step 302, sensor data indicative of a measure of activity performed and rest taken by the user is collected as a function of time. The sensor data is collected using at least one sensor of a device worn by the user.

Figure 4:
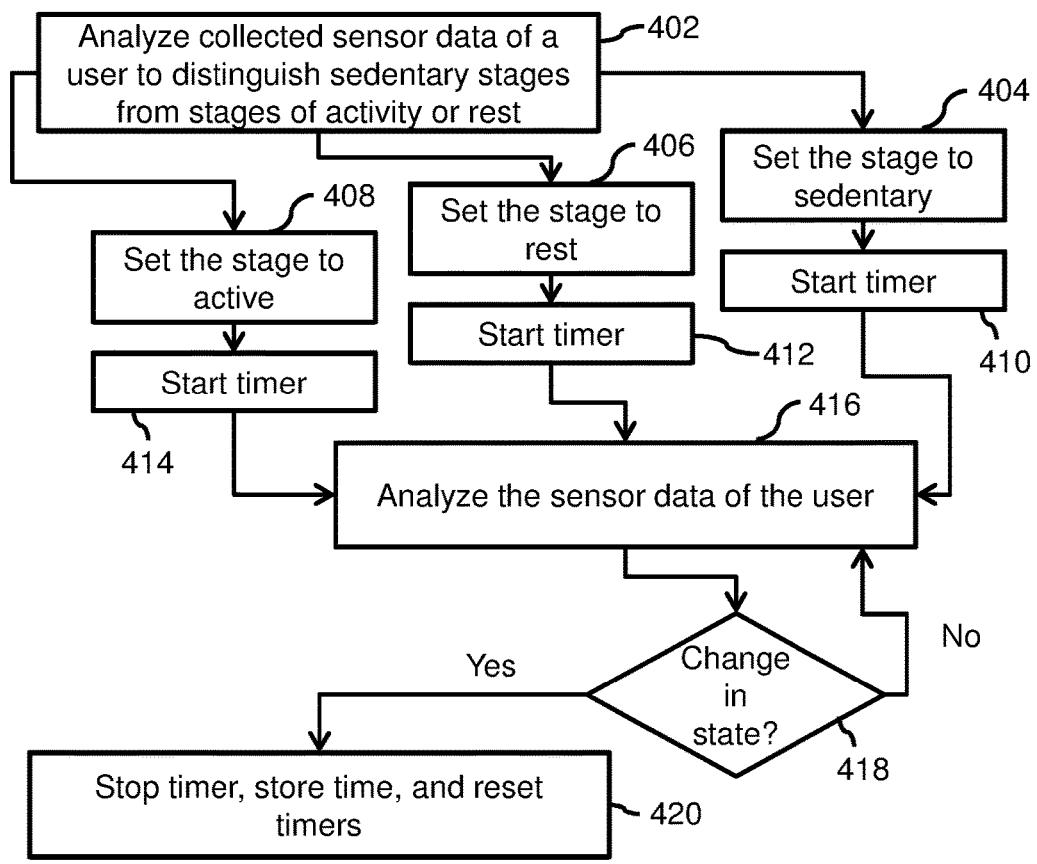
FIG. 4 is a flow chart for analyzing sensor data to distinguish sedentary stages from stages of activity or rest, in accordance with an embodiment of the present disclosure.

At step 304, the sensor data is analyzed to distinguish sedentary stages from stages of activity or rest (which is further explained in detail in conjunction with FIG. 4).

At step 306, a level is assigned to a given stage of activity or rest. The assigning of the level includes assigning a high intensity level to the given stage of activity or rest, when the intensity of activity exceeds a first threshold of intensity. Further, this step includes assigning a medium intensity level to the given stage of activity or rest, when the intensity of activity lies between the first threshold of intensity and a second threshold of intensity and the first threshold of intensity is greater than the second threshold of intensity. Moreover, this step includes assigning a very-low intensity level to the given stage of activity or rest, when the intensity of activity does not exceed the second threshold of intensity.

At step 308, a plurality of activity-rest parameters is evaluated for the user. The plurality of activity-rest parameters comprise at least one of a number of recovery days within a first predetermined time period, and a number of days elapsed from most recent recovery day. The recovery day is a day when time spent in activities of the high intensity level does not exceed a first threshold time and/or time spent in activities of the medium intensity level does not exceed a second threshold time.

At step 310, an activity-rest score is calculated from the plurality of activity-rest parameters, so as to provide a feedback indicating a status of the balance between physical activity and rest.

The steps 302 to 310 are only illustrative and other alternatives can also be provided where one or more steps are added, one or more steps are removed, or one or more steps are provided in a different sequence without departing from the scope of the claims herein. For example, in the method 300 the plurality of activity-rest parameters further comprise at least one of time spent in sedentary stages during a second predetermined time period; a number of sedentary alerts received during the second predetermined time period; a number of days, within the first predetermined time period, when the user has achieved a preset activity target; a sum of a first integral of a measure of intensity over time for activities of the high intensity level performed during the first predetermined time period and a second integral of the measure of intensity over time for activities of the medium intensity level performed during the first predetermined time period; and a number of days, within the first predetermined time period, when the sum of the first and second integrals exceeds a threshold value.

Further, in the method 300 the first predetermined time period is selected from the group consisting of last three days, last seven days, last 10 days, last two weeks and last month. Furthermore, in the method 300 the second predetermined time period is selected from the group consisting of last 24 hours, last 48 hours and last 72 hours. Moreover, in the method 300 the evaluation of the plurality of activity-rest parameters is performed based upon at least one of: an age of the user, a gender of the user, a weight of the user, a height of the user. Also, in the method 300 at least one of the plurality of activity-rest parameters contributes positively to the activity-rest score, and at least one of the plurality of activity-rest parameters contributes negatively to the activity-rest score. Additionally, in the method 300 the activity-rest score depends linearly on at least one of the plurality of activity-rest parameters. Alternatively, in the method 300 the activity-rest score depends non-linearly on at least one of the plurality of activity-rest parameters. The method 300 further comprises rendering the feedback on a display, so as to enable the user to see his/her performance with respect to each of the plurality of activity-rest parameters. The method 300 also comprises enabling the user to simulate how the activity-rest score changes when a given activity-rest parameter is changed.

Referring now to FIG. 4, illustrated is a flow chart 400 for analyzing the sensor data to distinguish the sedentary stages (or states) from stages of activity or rest, in accordance with an embodiment of the present disclosure.

At step 402, the collected sensor data of the user (such as the user 102 of FIG. 1) is analyzed to distinguish the sedentary stages from the stages of activity or rest. Further, at steps 404, 406 and 408 the wearable electronic device (such as the wearable electronic device 104 of FIG. 1) is set to a sedentary stage, an activity stage and a rest stage, respectively. Thereafter, at steps 410, 412 and 414 a timer of the wearable electronic device is started subsequent to setting the wearable electronic device in the sedentary stage at step 404, the activity stage at step 406 and the rest stage at step 408, respectively. Further, at step 416, again the sensor data of the user is analyzed. Thereafter, at step 418, it is checked that if there is any change in stage. If there is any change in the stage, then at step 420, the timer is stopped, time is stored and the timers are reset. If there is no change in the stage, the step 416 is performed further.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

What is claimed is:

1. A method for defining a balance between physical activity and rest for a user, the method comprising, using a processor to:
    collect sensor data indicative of a measure of activity performed and rest taken by the user as a function of time, wherein the sensor data is collected using at least one sensor of a device worn by the user, the at least one sensor of the device worn by the user being communicatively coupled to the processor, wherein the processor is further configured to:
    analyze the sensor data to distinguish sedentary stages from stages of activity or rest;
    assign a level to a given stage of activity or rest, wherein the assigning the level comprises
        (i) assigning a high intensity level to the given stage of activity or rest, when the intensity of activity exceeds a first threshold of intensity,
        (ii) assigning a medium intensity level to the given stage of activity or rest, when the intensity of activity lies between the first threshold of intensity and a second threshold of intensity, wherein the first threshold of intensity is greater than the second threshold of intensity, and
        (iii) assigning a very-low intensity level to the given stage of activity or rest, when the intensity of activity does not exceed the second threshold of intensity;
    evaluate a plurality of activity-rest parameters for the user, wherein the plurality of activity-rest parameters comprise at least one of:
        (a) a number of recovery days within a first predetermined time period, wherein a recovery day is a day when time spent in activities of the high intensity level does not exceed a first threshold time and/or time spent in activities of the medium intensity level does not exceed a second threshold time,
        (b) a number of days elapsed from most recent recovery day;
    calculate an activity-rest score from the plurality of activity-rest parameters, so as to provide a feedback indicating a status of the balance between the physical activity and the rest; and
    render the calculated activity-rest score on a user interface of a user device.

2. A method according to claim 1, wherein the plurality of activity-rest parameters further comprise at least one of:
    (c) time spent in sedentary stages during a second predetermined time period,
    (d) a number of sedentary alerts received during the second predetermined time period,
    (e) a number of days, within the first predetermined time period, when the user has achieved a preset activity target,
    (f) a sum of a first integral of a measure of intensity over time for activities of the high intensity level performed during the first predetermined time period and a second integral of the measure of intensity over time for activities of the medium intensity level performed during the first predetermined time period, and
    (g) a number of days, within the first predetermined time period, when the sum of the first and second integrals exceeds a threshold value.

3. A method according to claim 1, wherein the first predetermined time period is selected from a group consisting of last three days, last seven days, last 10 days, last two weeks and last month.

4. A method according to claim 1, wherein the second predetermined time period is selected from a group consisting of last 24 hours, last 48 hours and last 72 hours.

5. A method according to claim 1, wherein the evaluation of the plurality of activity-rest parameters is performed based upon at least one of: an age of the user, a gender of the user, a weight of the user, a height of the user, the quality of sleep of the preceding rest period, the quantity of sleep of the preceding rest period.

6. A method according to claim 1, wherein at least one of the plurality of activity-rest parameters contributes positively to the activity-rest score, and at least one of the plurality of activity-rest parameters contributes negatively to the activity-rest score.

7. A method according to claim 1, wherein the activity-rest score depends linearly on at least one of the plurality of activity-rest parameters.

8. A method according to claim 1, wherein the activity-rest score depends non-linearly on at least one of the plurality of activity-rest parameters.

9. A method according to claim 1, further comprising rendering the feedback on a display, so as to enable the user to see his/her performance with respect to each of the plurality of activity-rest parameters.

10. A method according to claim 1, further comprising enabling the user to simulate how the activity-rest score changes when a given activity-rest parameter is changed.

11. A system for defining a balance between physical activity and rest for a user, the system comprising:
   a sensor unit configured to be worn by the user and for collecting sensor data indicative of a measure of activity performed and rest taken by the user as a function of time, wherein the sensor data is configured to be collected by the sensor unit when the sensor unit is worn by the user; and
   a data processing arrangement coupled in communication with the sensor unit, wherein the data processing arrangement is configured to:
      analyze the sensor data received from the sensor unit to distinguish sedentary stages from stages of activity or rest,
      assign a level to a given stage of activity or rest, wherein when assigning the level, the data processing arrangement is configured to
         (i) assign a high intensity level to the given stage of activity or rest, when the intensity of activity exceeds a first threshold of intensity,
         (ii) assign a medium intensity level to the given stage of activity or rest, when the intensity of activity lies between the first threshold of intensity and a second threshold of intensity, wherein the first threshold of intensity is greater than the second threshold of intensity, and
         (iii) assign a very-low intensity level to the given stage of activity or rest, when the intensity of activity does not exceed the second threshold of intensity,
      evaluate a plurality of activity-rest parameters for the user, wherein the plurality of activity-rest parameters comprise at least one of:
         (a) a number of recovery days within a first predetermined time period, wherein a recovery day is a day when time spent in activities of the high intensity level does not exceed a first threshold time and/or time spent in activities of the medium intensity level does not exceed a second threshold time, and
         (b) a number of days elapsed from most recent recovery day,
      calculate an activity-rest score from the plurality of activity-rest parameters, so as to provide a feedback indicating a status of the balance between physical activity and rest; and
      render the calculated activity-rest score on a user interface of a user device.

12. A system according to claim 11, wherein the plurality of activity-rest parameters further comprise at least one of:
   (c) time spent in sedentary stages during a second predetermined time period,
   (d) a number of sedentary alerts received during the second predetermined time period,
   (e) a number of days, within the first predetermined time period, when the user has achieved a preset activity target,
   (f) a sum of a first integral of a measure of intensity over time for activities of the high intensity level performed during the first predetermined time period and a second integral of the measure of intensity over time for activities of the medium intensity level performed during the first predetermined time period, and
   (g) a number of days, within the first predetermined time period, when the sum of the first and second integrals exceeds a threshold value.

13. A system according to claim 11, wherein the first predetermined time period is selected from a group consisting of last three days, last seven days, last 10 days, last two weeks and last month.

14. A system according to claim 11, wherein the second predetermined time period is selected from a group consisting of last 24 hours, last 48 hours and last 72 hours.

15. A system according to claim 11, wherein the data processing arrangement is configured to evaluate the plurality of activity-rest parameters based upon at least one of: an age of the user, a gender of the user, a weight of the user, a height of the user, the quality of sleep of the preceding rest period, the quantity of sleep of the preceding rest period.

16. A system according to claim 11, wherein at least one of the plurality of activity-rest parameters contributes positively to the activity-rest score, and at least one of the plurality of activity-rest parameters contributes negatively to the activity-rest score.

17. A system according to claim 11, further comprising a display coupled to the data processing arrangement, wherein the data processing arrangement is further configured to render the feedback on the display, so as to enable the user to see his/her performance with respect to each of the plurality of activity-rest parameters.

18. A system according to claim 11, wherein the data processing arrangement is further configured to enable the user to simulate how the activity-rest score changes when a given activity-rest parameter is changed.

19. A computer program product comprising a non-transitory machine-readable data storage medium having stored thereon program instructions that, when accessed by a processing device, cause the processing device to:
   receive sensor data from a sensor device configured to collect physiological data of a user while the sensor device is being worn by the user, the sensor data being indicative of a measure of activity performed and rest taken by a user as a function of time, wherein the sensor data is collected using at least one sensor of a device worn by the user;
   analyze the sensor data to distinguish sedentary stages from stages of activity or rest;
   assign a level to a given stage of activity or rest by
      (i) assigning a high intensity level to the given stage of activity or rest, when the intensity of activity exceeds a first threshold of intensity,
      (ii) assigning a medium intensity level to the given stage of activity or rest, when the intensity of activity lies between the first threshold of intensity and a second threshold of intensity, wherein the first threshold of intensity is greater than the second threshold of intensity, and (iii) assigning a very-low intensity level to the given stage of activity or rest, when the intensity of activity does not exceed the second threshold of intensity;

evaluate a plurality of activity-rest parameters for the user, wherein the plurality of activity-rest parameters comprise at least one of:

(a) a number of recovery days within a first predetermined time period, wherein a recovery day is a day when time spent in activities of the high intensity level does not exceed a first threshold time and/or time spent in activities of the medium intensity level does not exceed a second threshold time, and (b) a number of days elapsed from a most recent recovery day;

calculate an activity-rest score from the plurality of activity-rest parameters, so as to provide a feedback indicating a status of the balance between physical activity and rest; and render the calculated activity-rest score on a user interface of a user device.

20. A computer program product according to claim 19, wherein the plurality of activity-rest parameters further comprise at least one of:

(c) time spent in sedentary stages during a second predetermined time period, (d) a number of sedentary alerts received during the second predetermined time period, (e) a number of days, within the first predetermined time period, when the user has achieved a preset activity target, (f) a sum of a first integral of a measure of intensity over time for activities of the high intensity level performed during the first predetermined time period and a second integral of the measure of intensity over time for activities of the medium intensity level performed during the first predetermined time period, and (g) a number of days, within the first predetermined time period, when the sum of the first and second integrals exceeds a threshold value.

21. The method according to claim 1, wherein the processor is further configured to render a graphical image of a slidable bar on the user interface, a movement of the slidable bar configured to configured to cause the processor to update the user interface with a prior calculated rest-activity score and corresponding activity-rest parameters associated with a particular date that the slidable bar points to in order to enable a comparison of date-based calculated rest-activity scores and corresponding activity-rest parameters.

22. The method according to claim 1, wherein the processor is configured to render the plurality of activity-rest parameters as graphical scales on the user interface and associate one or more of the graphical scales with a graphical image of a slidable bar, wherein the processor is configured to move the slidable bar in response to a detected input in order present a value of a corresponding activity-rest parameter on a day selected by the movement of the slidable bar.

* * * * *